(12) United States Patent
Lang et al.

(10) Patent No.: US 7,516,845 B2
(45) Date of Patent: Apr. 14, 2009

(54) MEDICAL DEVICE PACKAGE WITH DEFORMABLE PROJECTIONS

(75) Inventors: David K. Lang, Inverness (GB); Gordon G Sansom, Inverness (GB); Jerry Pugh, Mountain View, CA (US); Bryan Windus-Smith, Moray (GB); Emma Vanessa Jayne Day, Nairn (GB); Gregory Jean Paul Eldin, Tramoyes (FR)

(73) Assignee: Inverness Medical Limited (GB)

( * ) Notice: Subject to any disclaimer, the term of this patent is extended or adjusted under 35 U.S.C. 154(b) by 929 days.

(21) Appl. No.: 10/816,002

(22) Filed: Mar. 31, 2004

(65) Prior Publication Data

US 2005/0218024 A1    Oct. 6, 2005

(51) Int. Cl.
*B01L 11/00* (2006.01)
*B65D 83/10* (2006.01)
*A61B 17/32* (2006.01)

(52) U.S. Cl. .................. 206/438; 206/352; 206/363; 606/167; 30/335; 29/428

(58) Field of Classification Search ............... 206/438, 206/363, 352, 354, 359; 30/335; 606/167; 29/428
See application file for complete search history.

(56) References Cited

U.S. PATENT DOCUMENTS

| | | | | |
|---|---|---|---|---|
| 4,180,162 A | * | 12/1979 | Magney | 206/363 |
| 4,294,355 A | | 10/1981 | Jewusiak et al. | |
| 4,395,807 A | * | 8/1983 | Eldridge et al. | 29/239 |
| 4,845,923 A | * | 7/1989 | Donovan | 53/431 |
| 4,985,034 A | * | 1/1991 | Lipton | 606/167 |
| 5,046,611 A | | 9/1991 | Oh | |
| 5,230,428 A | * | 7/1993 | McShane | 206/363 |
| 5,363,958 A | | 11/1994 | Horan | |
| 5,720,924 A | | 2/1998 | Eikmeier et al. | |
| 5,863,800 A | | 1/1999 | Eikmeier et al. | |
| 5,875,532 A | | 3/1999 | Musgrave et al. | |
| 6,217,701 B1 | | 4/2001 | Shelley et al. | |
| 6,247,604 B1 | | 6/2001 | Taskis et al. | |
| 6,273,941 B1 | | 8/2001 | Law | |
| 6,324,896 B1 | | 12/2001 | Aoyagi | |
| 6,378,702 B1 | | 4/2002 | Kintzig | |
| 6,497,845 B1 | | 12/2002 | Sacherer | |
| 6,531,197 B2 | | 3/2003 | Neteler | |
| 2002/0014305 A1 | | 2/2002 | Dick et al. | |
| 2002/0017472 A1 | | 2/2002 | Weisshaupt | |

(Continued)

FOREIGN PATENT DOCUMENTS

EP    0824480 B1    1/2001

(Continued)

OTHER PUBLICATIONS

Letter dated Mar. 18, 2008 from Becerril, Coca & Becerril, Mexico, re Mexican Application No. PA/A/2005/003370.

*Primary Examiner*—Mickey Yu
*Assistant Examiner*—Jerrold Johnson

(57) ABSTRACT

A medical device package includes a body with at least one chamber therein, a proximal end and a distal end. The medical device package also includes at least one deformable projection within the chamber(s). Furthermore, the deformable projection is configured to deform resiliently upon contact with a medical device during insertion of the medical device into the chamber and, thereby, removably retain the medical device within the chamber.

4 Claims, 14 Drawing Sheets

U.S. PATENT DOCUMENTS

2003/0036200 A1  2/2003  Charlton

FOREIGN PATENT DOCUMENTS

| | | | |
|---|---|---|---|
| EP | 1118552 | A2 | 7/2001 |
| EP | 1118858 | A1 | 7/2001 |
| EP | 1285695 | A2 | 2/2003 |
| EP | 1288251 | A2 | 3/2003 |
| WO | WO 99/62697 | A1 | 12/1999 |
| WO | WO 00/13986 | A1 | 3/2000 |
| WO | WO 01/26782 | A1 | 4/2001 |
| WO | WO 01/64105 | A1 | 9/2001 |
| WO | WO 01/87731 | A2 | 11/2001 |
| WO | WO 02/49507 | A1 | 6/2002 |
| WO | WO 03/015627 | A2 | 2/2003 |

* cited by examiner

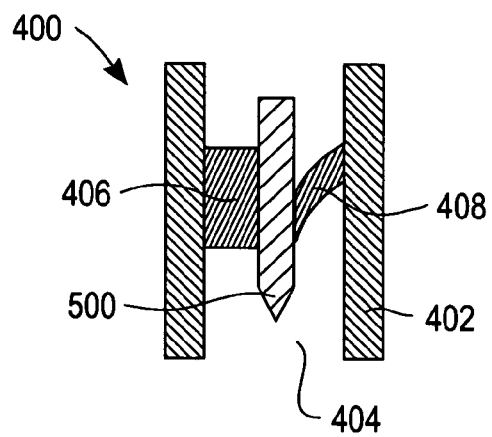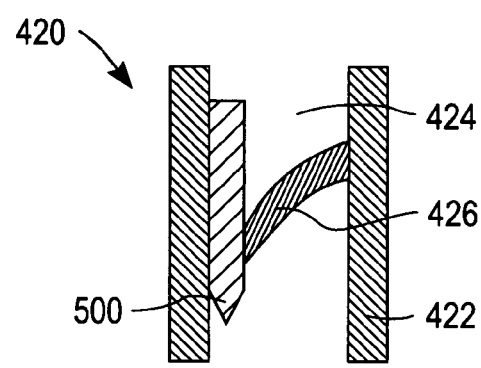
FIG. 10A        FIG. 10B
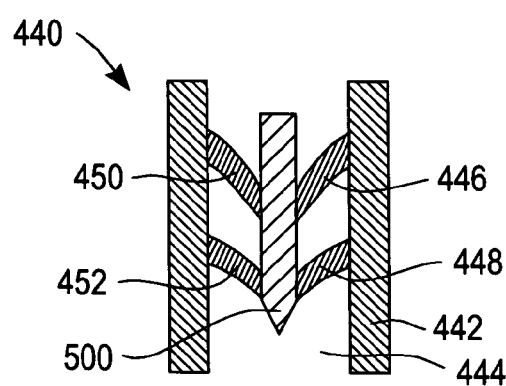
FIG. 10C

MEDICAL DEVICE PACKAGE WITH DEFORMABLE PROJECTIONS

BACKGROUND OF THE INVENTION

1. Field of the Invention

The present invention relates, in general, to medical device packages and, in particular, to medical device packages for receiving, and removably retaining, a medical device.

2. Description of the Related Art

A variety of medical devices require packaging to, for example, protect the medical device from damage prior to use and to maintain sterility of the medical device. For integrated medical devices that combine a dermal tissue penetration member (e.g., a lancet or micro-needle) with a test strip, the associated package should provide for an uncomplicated deployment of the dermal tissue penetration member during use, while also providing for protection of a user from inadvertent contact with the dermal tissue penetration member prior and subsequent to use. Furthermore, the packaging should provide humidity resistance for the test strip during storage.

Single-use (i.e., disposable) integrated medical devices are illustrative of the above requirements in that they require a medical device package that maintains sterility and protects the single-use integrated medical device contained therein from damage prior to use. Such medical device packages should also provide humidity resistance and UV protection for a test strip of single-use integrated medical devices prior to use. Furthermore, the medical device package should provide for deployment of a dermal tissue penetration member of such a single-use integrated medical device during use, as well as for disabling (i.e., preventing subsequent use) and safely discarding the single-use integrated medical device following use.

Conventional medical device packages do not fulfill all or even most of the requirements described above in a cost effective and/or efficient manner. Still needed in the field, therefore, is a medical device package that provides a sterility barrier and/or for protection of a medical device enclosed therein, while also providing for an uncomplicated deployment of the medical device during use. Furthermore, for integrated medical devices that include a dermal tissue penetration member (e.g., a lancet or micro-needle), a need exists for a medical device package that protects the dermal tissue penetration member from damage, humidity, and/or contamination prior to use, that protects a user from accidental contact therewith and that also disables the medical device following use, thereby preventing its repeated use. In addition, the materials and methods used to manufacture the medical device package should be cost effective.

SUMMARY OF THE INVENTION

Medical device packages according to embodiments of the present invention provide a sterility barrier and/or for protection of a medical device enclosed therein, while also providing for an uncomplicated deployment of the medical device during use. Medical device packages according to embodiments of the present invention also protect a user from accidental contact with the medical device and serve to disable the medical device following use. Furthermore, embodiments of medical device packages according to the present invention can be manufactured in a cost effective manner.

A medical device package according to embodiments of the present invention includes a body with at least one chamber defined therein and at least one deformable projection within the chamber. The at least one deformable projection is configured to deform resiliently upon contact with a medical device during insertion of the medical device at least partially within the chamber. Such a resilient deformation results in the medical device being securely, yet removably, retained within the chamber. In addition, the deformable projection(s) securely holds a medical device in a predetermined orientation and location such that the medical device can be easily deployed (e.g., extracted) from the chamber.

The combination of body and deformable projections provide a medical device package that protects a medical device contained therein from damage during insertion, containment and extraction of the medical device.

A method for extracting a medical device from a medical device package according to an exemplary embodiment of the present invention includes providing a medical device package, with a medical device contained therein, and a connector. The provided medical device package includes a body with at least one chamber defined therein. The medical device package also includes at least one deformable projection within the chamber(s), with the deformable projection(s) being configured to deform resiliently upon contact with a medical device during insertion of the medical device at least partially within the chamber and, thereby, removably retain the medical device at least partially within the chamber.

The method also includes the steps of inserting at least a portion of the connector into the chamber, engaging the medical device with the connector, and extracting the engaged medical device from the chamber of the medical device package with the connector. Optionally, the connector can be employed to resiliently deform the deformable projection(s) either during engagement between the medical device and connector or subsequent to such engagement and prior to extraction of the engaged medical device.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings (wherein like numerals represent like elements), of which:

FIGS. 10A through 10C are simplified cross-sectional side views of a medical device package depicting various deformable projection configurations;

DETAILED DESCRIPTION OF THE INVENTION

Figure 1:
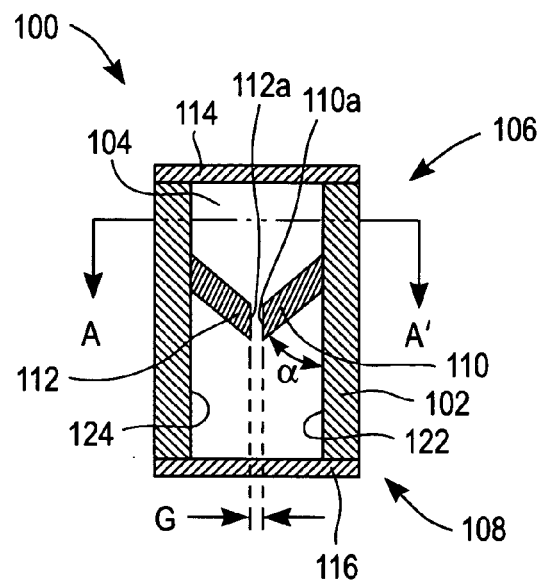
FIG. 1 is a simplified cross-sectional side view of a medical device package according to an exemplary embodiment of the present invention.
Figure 2:
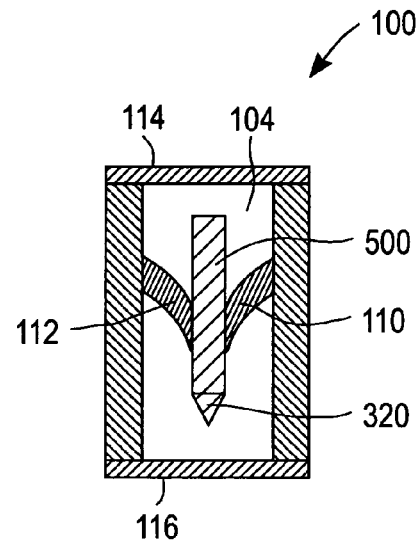
FIG. 2 is a simplified cross-sectional side view of the medical device package of FIG. 1 containing a medical device.
Figure 5:
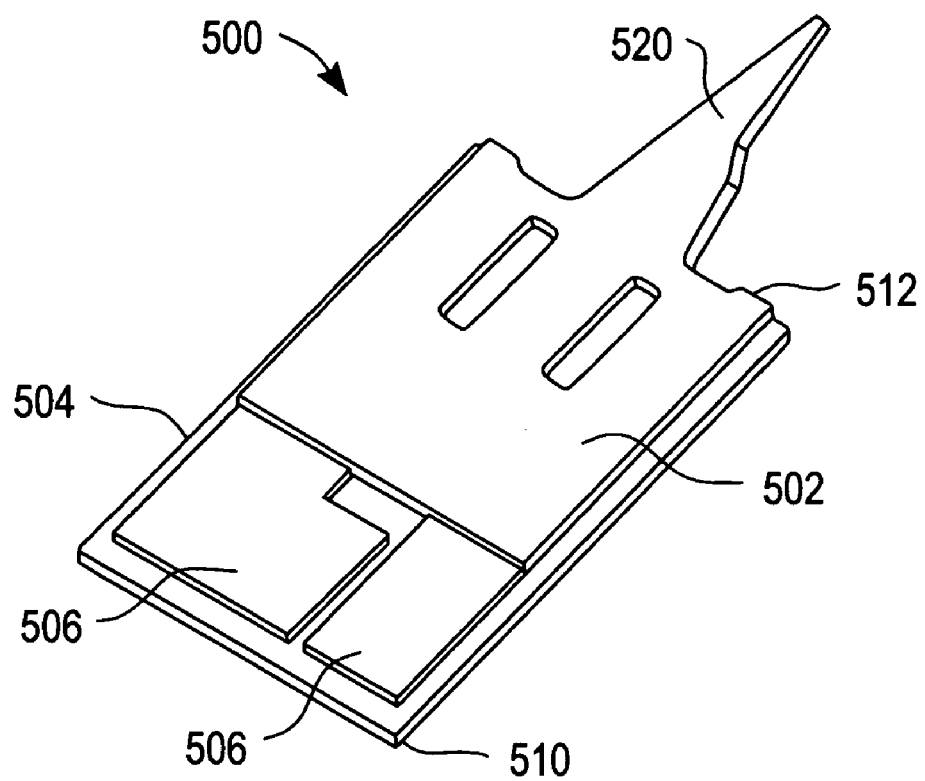
FIG. 5 is a simplified perspective view of a medical device that can be contained within exemplary embodiments of medical device packages according to the present invention.
Figure 6A:
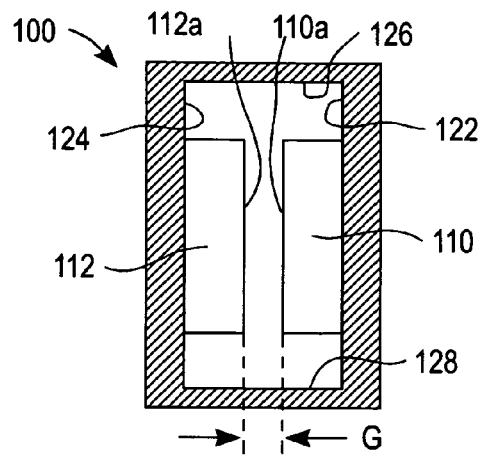
FIG. 6A is a simplified cross-sectional top view (as viewed along line A-A' in FIG. 1.) of the medical device package of FIG. 1.

FIGS. 1-4 are simplified depictions of a medical device package 100 according to an exemplary embodiment of the present invention. FIG. 5 is a simplified depiction of a medical device 500 that can be contained within medical device package 100. FIG. 6A is a simplified top cross-sectional view of medical device package 100. As discussed in detail below, medical device package 100 is configured to securely, yet removably, contain a medical device (such as medical device 500), as depicted in FIG. 2.

Referring to FIGS. 1-4 and 6A, medical device package 100 includes a body 102 with a chamber 104 defined therein. Body 102 has a proximal end 106 and a distal end 108. In addition, medical device package 100 includes first and second deformable projections 110 and 112, respectively, that are disposed within chamber 104. In the embodiment of FIGS. 1 and 2, medical device package 100 also includes a proximal cap member 114 and a distal cap member 116.

As depicted in FIG. 2, first and second deformable projections 110 and 112 are configured to deform resiliently upon contact with medical device 500 during insertion of medical device 500 into chamber 104 and, thereby, removably retain medical device 500 within chamber 104. Although FIG. 2 depicts medical device 500 as being completely inserted in chamber 104, one skilled in the art will recognize that medical device packages according to embodiments of the present invention could be configured such that a medical device is only partially inserted with a chamber and removably retained partially within the chamber.

Figure 3:
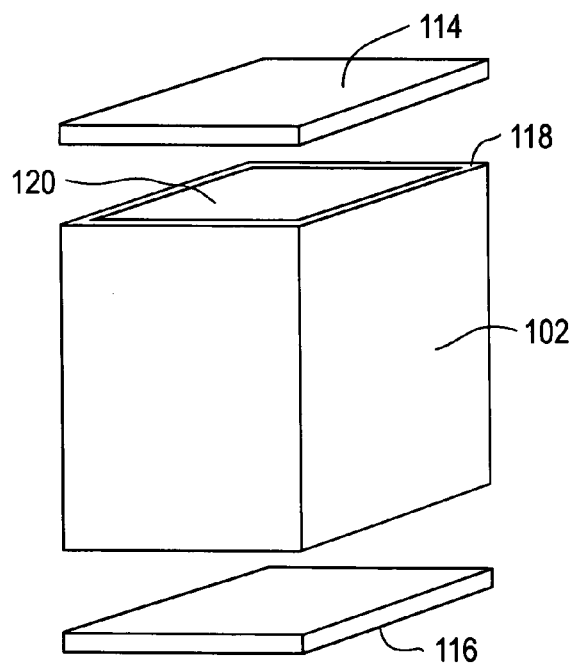
FIG. 3 is a simplified exploded perspective view of the body, proximal end cap member and distal end cap member of the medical device of FIG. 1.
Figure 4:
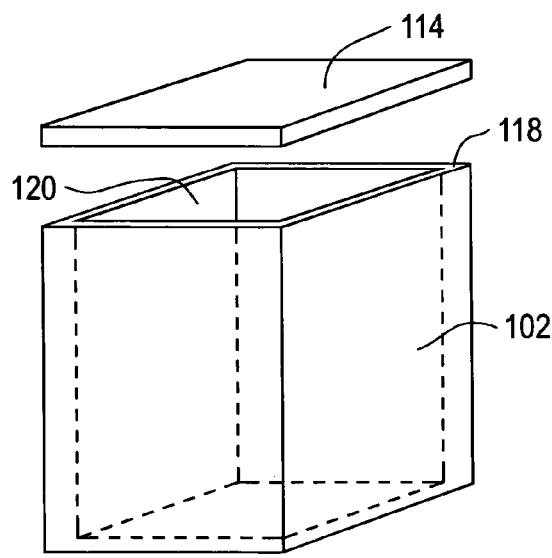
FIG. 4 is a simplified exploded perspective view of portions of the body and proximal cap member of the medical device package of FIG. 1, with dashed lines indicating features that are not visible in the perspective view of FIG. 4.

In the embodiment of FIGS. 1-4 and 6A, body 102 includes a rim 118 defining a proximal end aperture 120 (as shown in FIGS. 3 and 4), opposing first and second inner walls 122 and 124, and opposing third and fourth inner walls 126 and 128. First, second, third and fourth inner walls 122, 124, 126, and 128 define chamber 104. First deformable projection 110 is attached to first inner wall 122 of body 102. Second deformable projection 112 is attached to second inner wall 124 of body 102.

A gap G exists between the first and second deformable projections 110 and 112, as depicted in FIG. 1. In addition, first and second deformable projections 110 and 112 each form an angle $\alpha$ with first and second inner walls 122 and 124, respectively. Angle $\alpha$ can be any suitable angle, but angle $\alpha$ is typically less than 90 degrees, for example, in the range of from 20 degrees to 80 degrees. Lesser $\alpha$ angles may result in deformable projections that retain medical devices with a relatively weaker retaining force in comparison to deformable projections with greater $\alpha$ angles. However, deformable projections with lesser $\alpha$ angles may be more robust in terms of being able to retain medical devices with a wider range of sizes than deformable projections with greater $\alpha$ angles.

Medical device package 100 is configured to receive, and to securely and removably retain, a medical device (e.g., medical device 500 of FIG. 5), at least partially therein, as illustrated in FIG. 2 for a circumstance that the medical device is completely within the medical device package. In FIG. 2, medical device 500 is shown securely and removably retained between deformable projections 110 and 112 in chamber 104. Deformable projections 110 and 112 have been resiliently deformed, and angle $\alpha$ decreased, by the presence of medical device 500 in medical device package 100. Angle $\alpha$ enables first and second deformable projections 110 and 112 to beneficially act as guides when medical device 500 is inserted into chamber 104. First and second deformable projections 110 and 112 can, therefore, minimize the risk of damage to medical device 500 as it is loaded (i.e., inserted) into chamber 104.

FIG. 5 is a perspective view of medical device 500 that can, as previously noted, be securely and removably contained within medical device package 100. Medical device 500 includes a test strip 504 and a dermal tissue penetration member 502 and, therefore, can be considered an integrated medical device.

Test strip 504 has a reaction area (not shown) and electrical contacts 506 that terminate on a distal end 510 of medical device 500. Electrical contacts 506 are made of any suitable conductive material, such as carbon. Dermal tissue penetration member 502 includes a lancet 520 adapted to pierce a user's skin and draw blood into the reaction area of test strip 504. Further descriptions of integrated medical devices that can be contained within embodiments of medical device packages according to the present invention are in International Application No. PCT/GB01/05634 (published as WO 02/49507 on Jun. 27, 2002) and U.S. patent application Ser. No. 10/143,399, both of which are fully incorporated herein by reference. In addition, dermal tissue penetration member 502 can be fabricated, for example, by a progressive die-stamping technique, as disclosed in the aforementioned International Application No. PCT/GB01/05634 (published as WO 02/49507 on Jun. 27, 2002) and U.S. patent application Ser. No. 10/143,399.

Referring again to FIGS. 1 through 4, rim 118 includes sufficient surface area to enable proximal cap member 114 to be adhered to rim 118 by processes known to those skilled in the art, including, but not limited to, heat sealing processes. In this manner, proximal cap member 114, along with distal cap member 116 and body 102 of medical device package 100, provides a sterility barrier and ambient humidity protection for a medical device contained within the chamber of the medical device package.

Body 102 can be formed of any suitable material known to those of skill in the art including, for example, rigid plastic materials such as high density polyethylene (HDPE), polystyrene, polycarbonate and polyester. Such rigid plastic materials are impervious to puncturing and to air and/or air-borne bacteria and, therefore, provide a sterility barrier and a puncture-resistant protective barrier. It can be particularly beneficial in terms of humidity protection for body 102 to be formed of, or include, a layer of a desiccant-loaded high-density polyethylene (e.g., 2AP desiccant-loaded high-density polyethylene, commercially available from Airsec of France). Furthermore, carbon black can combined with a rigid material (e.g., a combination of carbon black and HDPE) to provide enhanced light protection capabilities to the body.

Proximal cap member 114 is configured to cover proximal end aperture 120 once a medical device has been received in chamber 104. Proximal cap member 114 (as well as distal cap member 116) can be, for example, a breachable film such as breachable metallic foil. Other suitable materials for proximal cap member 114 and/or distal cap member 116 include paper, polymer and Tyvek. Those skilled in the art will also recognize that proximal cap member 114 and/or distal cap member 116 can alternatively be rigid and/or re-closable.

First and second deformable projections 110 and 112 can be formed of resiliently and/or permanently deformable materials including, for example, polystyrene, polycarbonate, and polyester or elastomeric materials including silicone, Teflon, latex or other types of rubber. The use of a deformable material for the deformable projections is beneficial in that damage to a medical device during insertion, containment and removal is minimized.

The deformable projections can be optionally coated with a material that reduces the likelihood of damage to a medical device and improves the frictional grip between first and second deformable projections 110 and 112 and a medical device.

Referring to FIGS. 1 and 6A, first and second deformable projections 110 and 112 each include a projection surface 110a and 112a, respectively. Projection surfaces 110a and 112a can, for example, be smoothly curved with no sharp edges to reduce the likelihood of damage to a medical device. In addition, each of projection surfaces 110a and 112a can be optionally configured to contact a medical device (e.g., medical device 500) at more than one location so that the medical device is restricted from potentially damaging rotation, pivoting or sliding during storage or transit. Projection surfaces 110a and 112a also serve to guide a medical device away from first and second inner walls 122 and 124 during loading of the medical device into package 100, thereby preventing damage to the medical device due to collision with the first and second inner walls 122 and 124.

FIG. 2 is a cross-sectional view of medical device package 100 with medical device 500 retained therein prior to use of medical device 500 (i.e., prior to extraction of medical device 500 from the medical device package 100 for use). In FIG. 2, medical device 500 is disposed between first and second deformable projections 110 and 112 and is positioned substantially parallel to first and second walls 122 and 124. Medical device 500 is securely retained within cavity 104 via a frictional interaction with first and second deformable projections 110 and 112 (e.g., a combination of the coefficient of friction between the deformable projections and a retained medical device and a retaining force [e.g., a "squeezing" force] provided by the resilient nature of the deformable projections). Lancet 520 is retained within chamber 104 and, thus, protected from inadvertent damage.

Figure 6B:
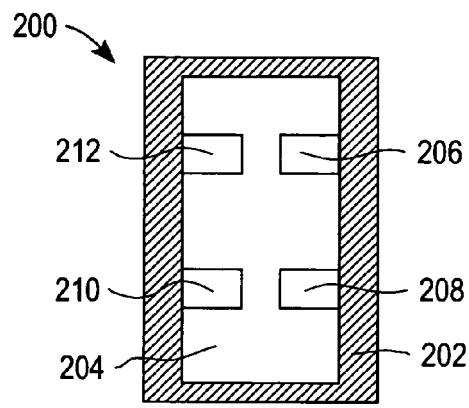
FIGS. 6B through 6E are simplified cross-sectional top views of medical device packages according to various exemplary embodiments of the present invention, with each of FIGS. 6B through 6E depicting alternative deformable projection configurations.
Figure 6C:
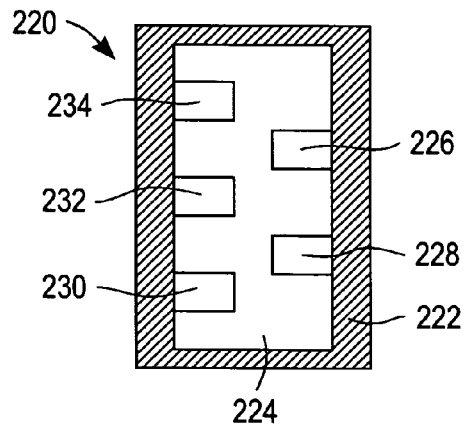

FIGS. 6B through 6E depict alternative exemplary configurations of deformable projections within a medical device package according to the present invention. FIG. 6B depicts a configuration 200 wherein a medical device package body 202 has a chamber 204 therein and the medical device package body 202 includes four deformable projections 206, 208, 210 and 212. FIG. 6C depicts a configuration 220 wherein a body 222 of a medical device package has a chamber 224 therein and the body 222 includes five staggered deformable projections 226, 228, 230, 232 and 234. The deformable projections of FIG. 6C are staggered in that deformable projections 226 and 228 are not in an opposing relationship with any of deformable projections 230, 232 and 234.

Figure 6D:
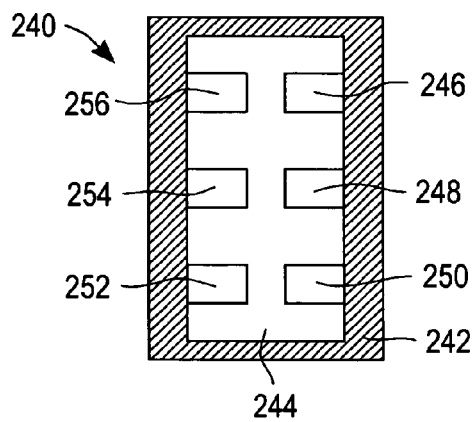
Figure 6E:
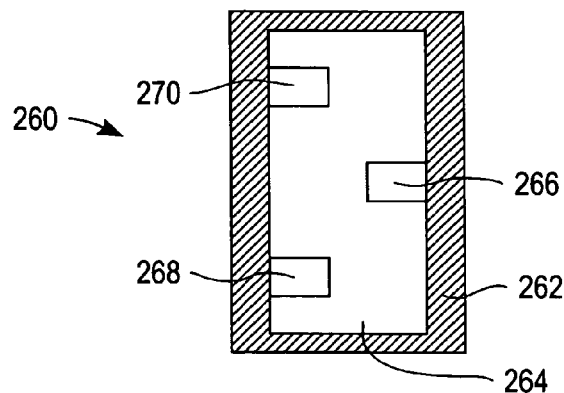

FIG. 6D depicts a configuration 240 wherein a medical device package body 242 has a chamber 244 therein and the medical device package body 242 includes six deformable projections 246, 248, 250, 252, 254 and 256. FIG. 6E depicts a configuration 260 wherein a medical device package body 262 has a chamber 264 therein and medical device package body 262 includes three staggered deformable projections 266, 268 and 270.

In each of the configurations of FIGS. 6B-6E, the deformable projections have been configured to securely and removably retain a medical device without any significant or deleterious deformation of the medical device. However, the deformable projections serve to prevent significant movement of a medical device within the medical device package, thus avoiding mechanical damage to the medical device.

Figure 7A:
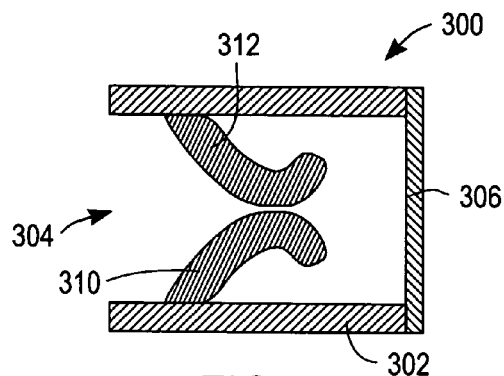
FIG. 7A is a simplified cross-sectional side view of a medical device package according to another embodiment of the present invention.
Figure 7B:
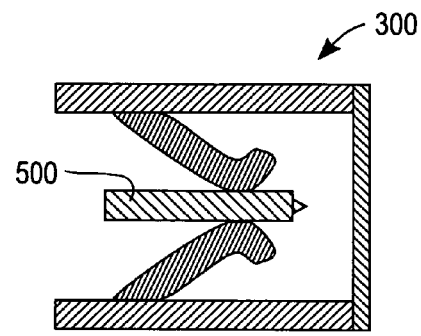
FIG. 7B is a simplified cross-sectional side view of the medical device package of FIG. 7A containing a medical device.

Referring to FIGS. 7A and 7B, medical device package 300 includes a body 302, with a chamber 304 defined therein, and a distal cap member 306. Medical device package 300 includes first and second deformable projections 310 and 312, respectively, that are disposed within chamber 304. First and second deformable projections 310 and 312 have a curved shape (with no sharp edges) that aids in preventing damage to a medical device during insertion, storage and removal from medical device package 300.

As a medical device 500 is inserted into medical device package 300, first and second deformable projections 310 and 312 flex to securely and removably retain medical device 500 (see FIG. 7B). The use of curved deformable projections facilitates insertion and extraction of a medical device by providing for the medical device to easily slide over these deformable projections.

Figure 8A:
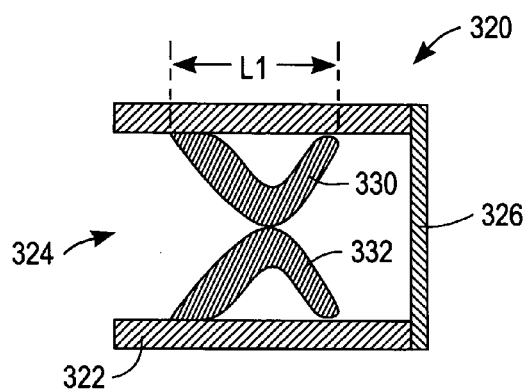
FIG. 8A is a simplified cross-sectional side view of a medical device package according to yet another embodiment of the present invention.
Figure 8B:
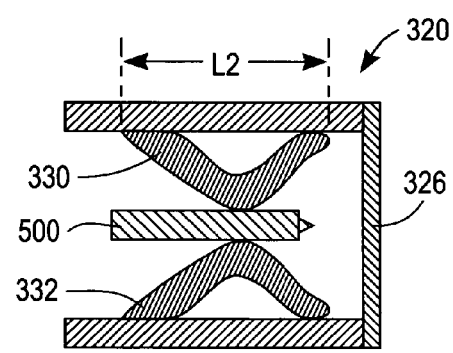
FIG. 8B is a simplified cross-sectional side view of the medical device package of FIG. 8A containing a medical device.

Referring to FIGS. 8A and 8B, medical device package 320 includes a body 322, with a chamber 324 defined therein, and a distal cap member 326. Medical device package 320 also includes first and second deformable projections 330 and 332, respectively, disposed within chamber 324. As a medical device (e.g., medical device 500 illustrated in FIG. 8B) is inserted into medical device package 320, first and second deformable projections 330 and 332 move longitudinally toward distal cap member 326 such that the distance L1 of FIG. 8A is increased to distance L2 of FIG. 8B. L1 can range, for example, from half to two-thirds the length of body 322. L2 can be, for example, 25% to 50% greater than L1 and in the range of from two-thirds to three-fourths the length of body 322. In the embodiment of FIGS. 8A and 8B, each of first and second deformable projections 330 and 332 contact body 322 at two points in order to enhance the physical stability of medical device retained within medical device package 320.

Figure 9A:
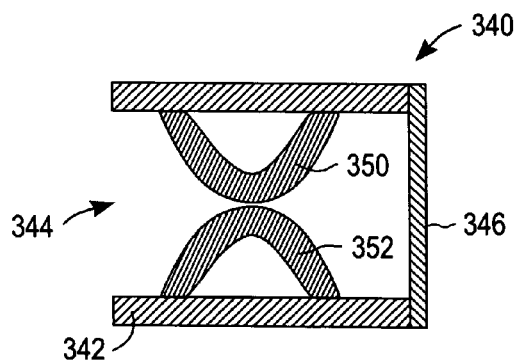
FIG. 9A is a simplified cross-sectional side view of a medical device package according to still another embodiment of the present invention.
Figure 9B:
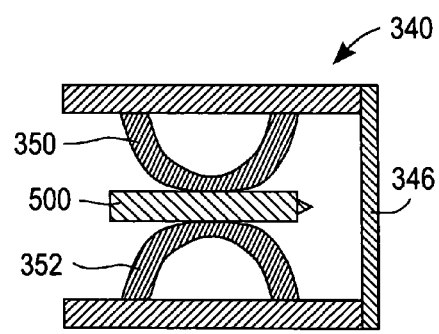
FIG. 9B is a simplified cross-sectional side view of the medical device package of FIG. 9A containing a medical device.
Figure 11:
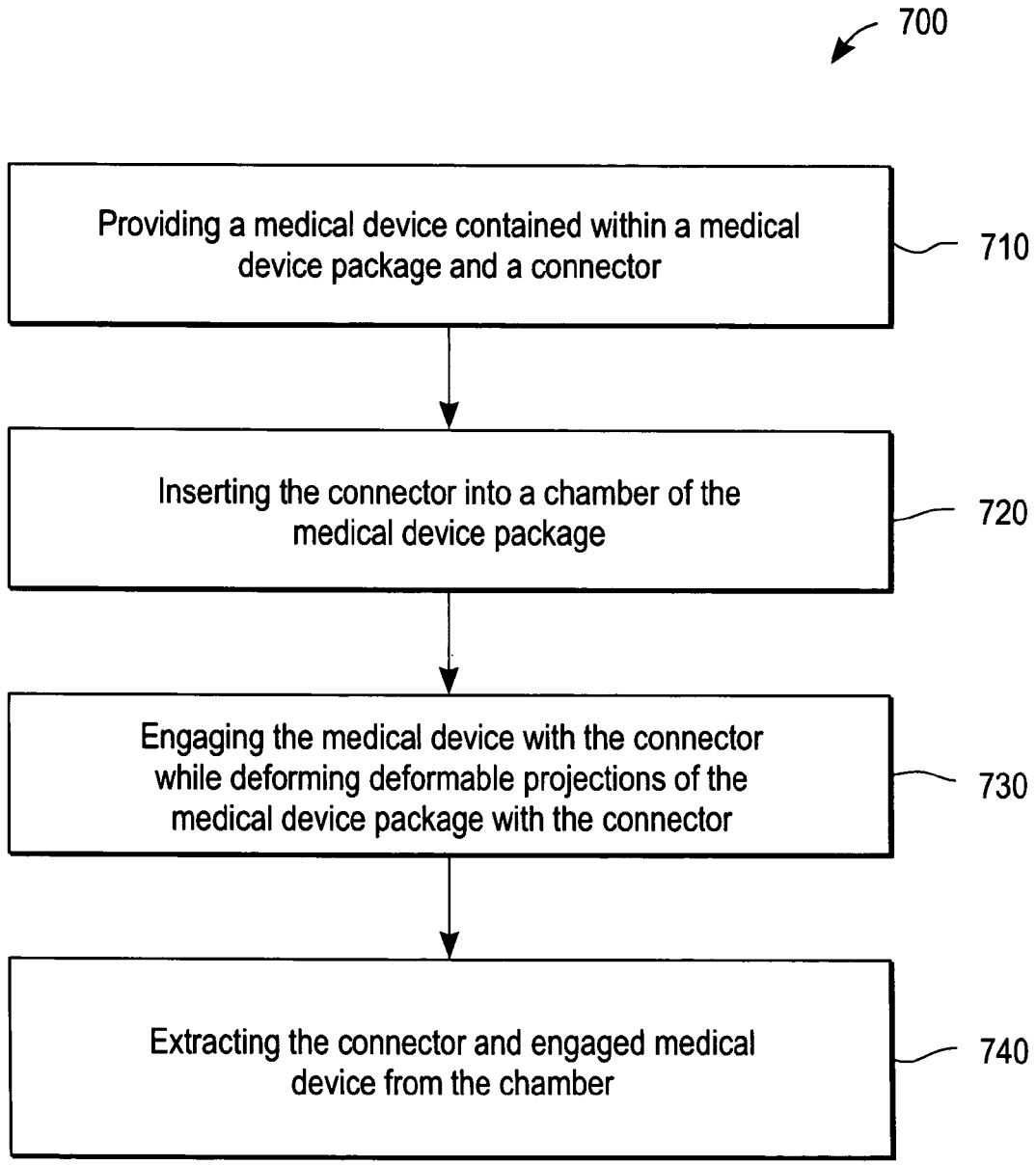
FIG. 11 is a flow chart illustrating a sequence of steps in a process for extracting a medical device from a medical device package according to an embodiment of the present invention.

Referring to FIGS. 9A and 9B, medical device package 340 includes a body 342, with a chamber 344 defined therein, and a distal cap member 346. Medical device package 340 also includes first and second deformable projections 350 and 352, respectively, disposed within chamber 344. As depicted in FIGS. 9A and 9B, each of first and second deformable projections 350 and 352 is configured and attached to body 342 to form a looped (e.g., roughly U-shaped) configuration. When a medical device is inserted into medical device package 340, the areas of contact between the medical device and each of first and second deformable projections 350 and 352 flatten such that relatively large areas of contact are made with medical device 500, facilitating the secure retention of the medical device within medical device package 340. Optionally, the first and second deformable projections could be configured such that each provides multiple points of contact with the medical device.

FIGS. 10A through 10C show various configurations of deformable projections within a medical device package according to the present invention. In each of FIGS. 10A through 10C, a medical device (i.e., medical device 500 of FIG. 5) is depicted as being securely and removably retained.

FIG. 10A depicts a configuration 400 wherein a medical device package body 402, with a chamber 404 therein, includes an elevation 406 and a deformable projection 408. The combination of deformable projection 408 and elevation 406 provides a relatively large area of contact between medical device 500 and elevation 406, thereby restricting movement of, and alleviating risk of damage to, medical device 500. Elevation 406 can be formed, for example, of either a rigid or a deformable material. In the circumstance that elevation 406 is formed of a rigid material, the position of a medical device within configuration 400 is accurately controlled since the medical device is retained against the rigid elevation by deformable projection 408.

FIG. 10B depicts a configuration 420 wherein a medical device package body 422, with a chamber 424 therein, includes a single deformable projection 426. In the embodiment of FIG. 10B, a medical device (i.e., medical device 500) is securely retained between deformable projection 426 and medical device package body 422. In this embodiment, the flat surface contact of the medical device package body 422 helps ensure that medical device 500 is securely and removably retained.

FIG. 10C depicts a configuration 440 wherein a medical device package body 442, with a chamber 444 therein, includes four deformable projections 446, 448, 450 and 452. The use of multiple deformable projections (for example, the four deformable projections of configuration 440) beneficially provides multiple contact surfaces to hold a medical device securely and to prevent damage to the medical device.

Further aspects of various embodiments of medical device packages according to the present invention are described hereafter in relation to various processes for removing (i.e., extracting) a medical device from a medical device package. For example, removal of medical device 500 can be accomplished using a connector 600 (see, for example, FIG. 12C described further below). Connector 600 is shaped and sized, and otherwise configured and adapted, to extract (i.e., remove) a medical device (e.g., medical device 500 of FIG. 5) from medical device packages according to exemplary embodiments of the present invention. In addition, connector 600 can advantageously be used to mechanically and/or manually manipulate such a medical device once the medical device has been extracted from the medical device package. For example, connector 600 can be used to transfer a medical device from a medical device package to a metering system. As will be appreciated by those skilled in the art, connector 600 may be a component (either a removable component or a permanently integrated component) of a metering system (e.g., an analytical meter configured to determine analyte concentrations in biological fluid samples). Alternatively, connector 600 can be combined with medical device packages to form a kit as described in co-pending U.S. patent application Ser. No. 10/666,154, which is hereby incorporated in full by reference.

FIGS. 11 and 12A-12C depict a process 700 for removing a medical device (i.e., medical device 500 of FIG. 5) from medical device package 100 of FIGS. 1-4. Process 700 includes first providing a medical device contained within medical device package 100 and a connector 600, as set forth in step 710 of FIG. 11 and depicted in FIG. 12A.

Next, at least a portion of connector 600 is inserted into chamber 104 of medical device package 100 (see step 720 of FIG. 11) by breaching proximal cap member 114. Connector 600 is then engaged with medical device 500. After connector 600 engages with medical device 500, connector 600 causes first and second deformable projections 110 and 112 to deform (see step 730 of FIG. 11 and the depiction of FIG. 12B). Connector 600 and engaged medical device 500 are then extracted from chamber 104 of medical device package 100, as set forth in step 740 of FIG. 11 and shown in FIG. 12C.

Figure 12A:
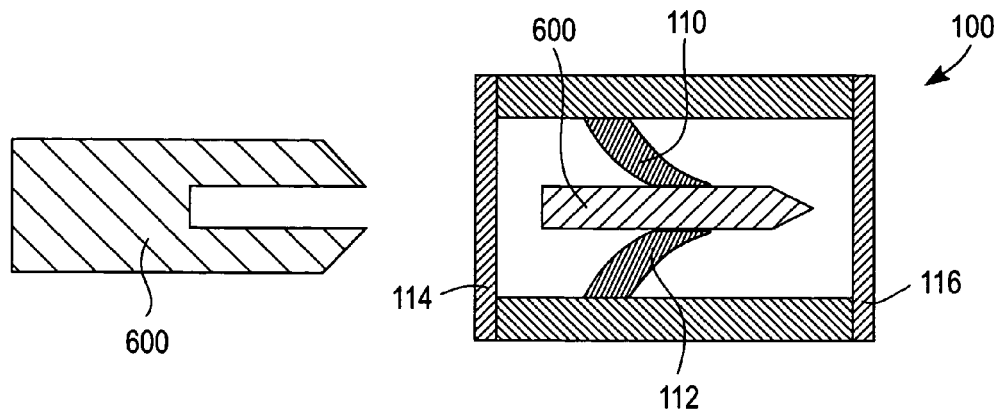
FIGS. 12A through 12C are schematic, cross-sectional side views depicting various stages of the process of FIG. 11.
Figure 12B:
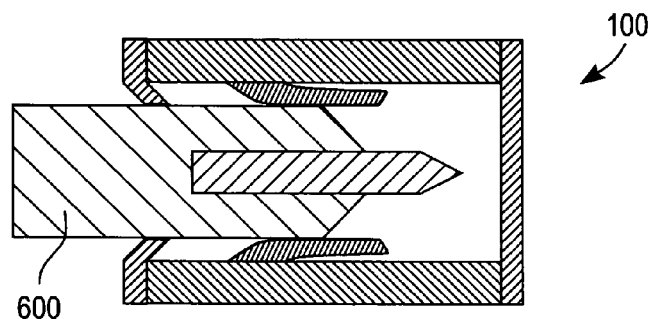
Figure 12C:
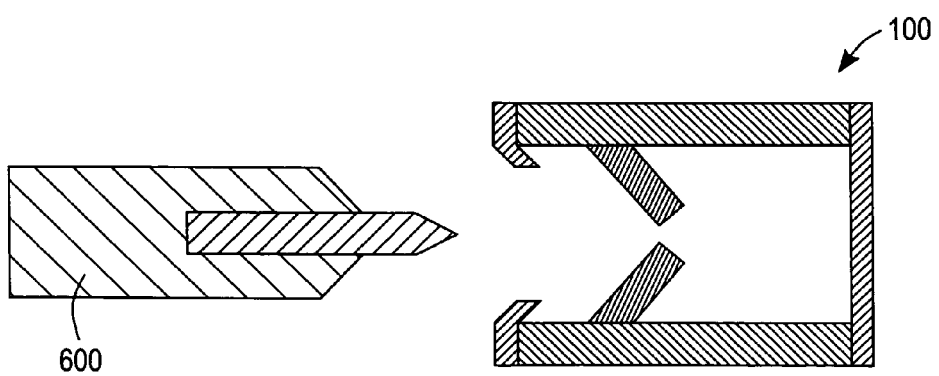
Figure 13:
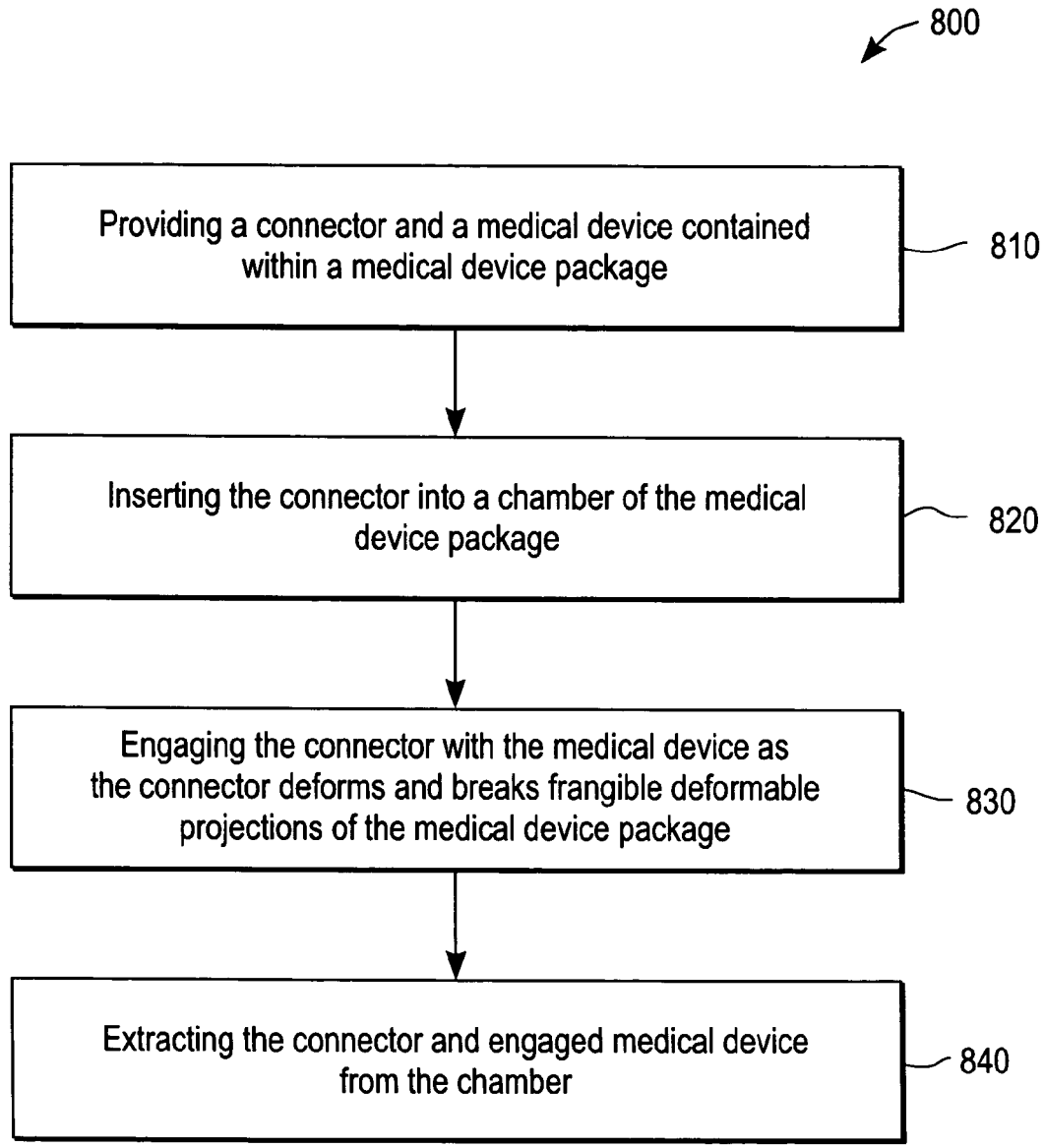
FIG. 13 is a flow chart illustrating a sequence of steps in a process for extracting a medical device from a medical device package that includes a frangible deformable projection according to another embodiment of the present invention.
Figure 14A:
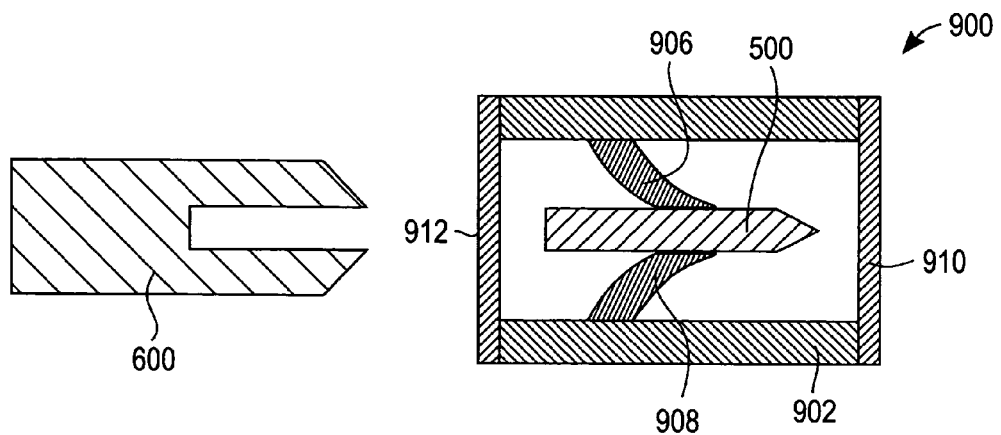
FIGS. 14A through 14C are schematic, cross-sectional views depicting various stages of the process of FIG. 13.
Figure 14B:
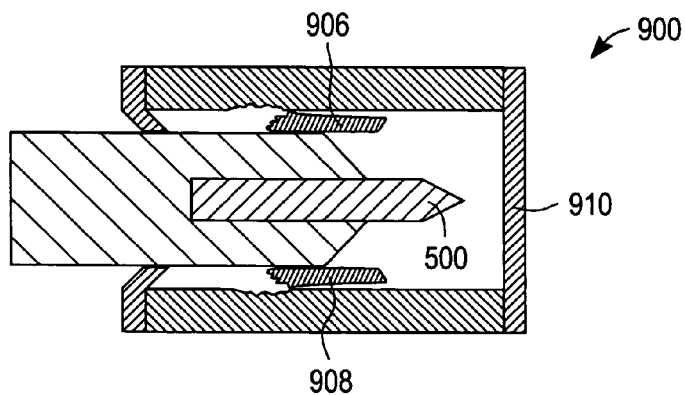
Figure 14C:
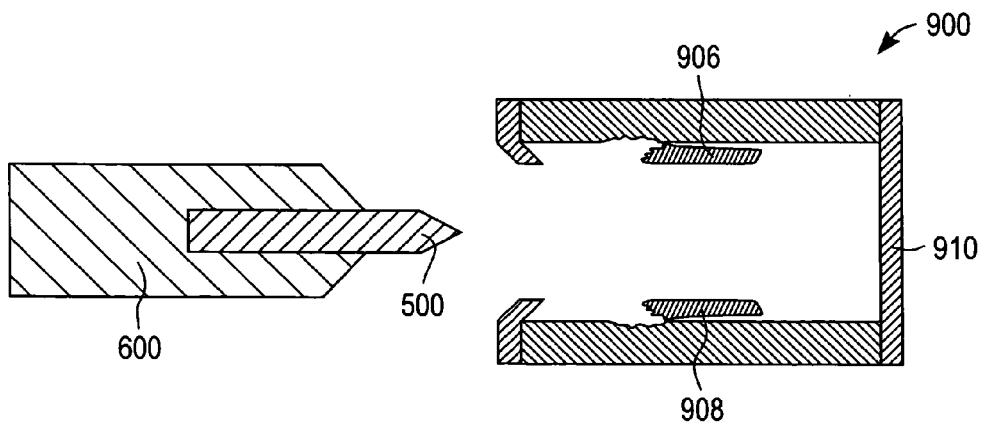

FIG. 12C illustrates a circumstance where connector 600 and medical device 500 are extracted through proximal cap member 114 (which had been previously breached in step 720). Alternatively, connector 600 could be used to extract engaged medical device 500 by pushing medical device 500 through distal cap member 116 (if distal cap member 116 is formed of a breachable material such as a metallic foil). Alternatively, the distal cap member can be removed prior to extraction of the medical device in order to avoid potential damage to the medical device during breaching of the distal cap member.

The force required for connector 600 to engage with the medical device in step 730 is, for example, approximately 2N. As the connector engages with the medical device, the deformable projections reversibly bend (i.e., deform) away from the medical device toward the body of the medical device package. Each of the steps of process 700 can be performed, for example, either manually by a user and/or with the aid of a mechanical and/or electrical device.

FIGS. 13 and 14A-14C depict a process 800 for removing a medical device (i.e., medical device 500 of FIG. 5) from a medical device package 900 according to an exemplary embodiment of the present invention. Process 800 includes first providing a medical device contained within medical device package 900 and a connector 600, as set forth in step 810 of FIG. 13 and depicted in FIG. 14A.

Medical device package 900 includes a body 902 with a chamber 904 defined therein. Medical device package 900 also includes first and second frangible deformable projections 906 and 908, respectively, a distal cap member 910 and a proximal cap member 912. First and second frangible deformable projections 906 and 908 are configured to deform resiliently upon contact with a medical device during insertion of the medical device at least partially within the chamber. Thereafter, first and second frangible deformable projections 906 and 908 removably retain the medical device within chamber 904. Furthermore, first and second frangible deformable projections 906 and 908 are also adapted to break upon a predetermined deformation (as described below with respect to step 830 and FIGS. 14B and 14C).

Next, at least a portion of connector 600 is inserted into chamber 904 of medical device package 900 (see step 820 of FIG. 13) by breaching proximal cap member 912. Connector 600 is then engaged with medical device 500. As connector 600 engages with medical device 500, connector 600 deforms first and second frangible deformable projections 906 and 908 to a predetermined point at which first and second frangible deformable projections 906 and 908 break free (either partially or fully) of body 902, as set forth in step 830 of FIG. 13 and depicted in FIG. 14B. Connector 600 and engaged medical device 500 are then extracted from chamber 904 of medical device package 900, as set forth in step 840 of FIG. 13 and shown in FIG. 14C.

Figure 15:
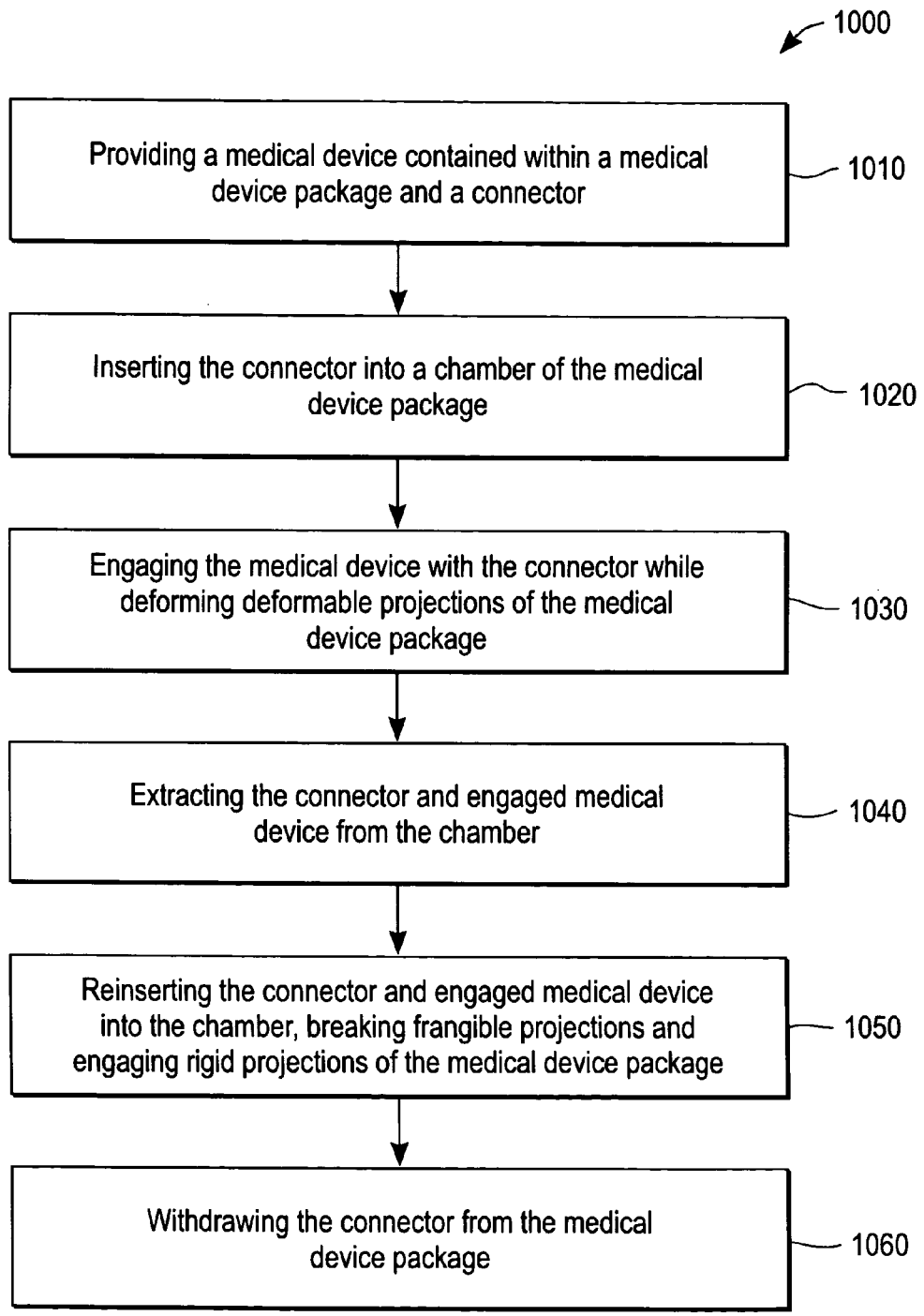
FIG. 15 is a flow chart illustrating a sequence of steps in a process for extracting a medical device from a medical device package and subsequently disabling the medical device according to an embodiment of the present invention.

FIG. 15 is a flow chart illustrating a sequence of steps in a process 1000 for extracting a medical device from a medical device package 1100 for use and subsequently disabling the medical device after use according to an exemplary embodiment of the present invention. Referring to FIGS. 15 and 16A through 16E, process 1000 includes first providing a medical device 510 contained within medical device package 1100 and a connector 610, as set forth in step 1010 of FIG. 15 and depicted in FIG. 16A.

Medical device package 1100 includes a body 1102 with a chamber 1104 defined therein. Medical device package 1100 also includes first and second deformable projections 1106 and 1108, respectively, a distal cap member 1110 and a proximal cap member 1112. First and second deformable projections 1106 and 1108 are configured to deform resiliently upon contact with a medical device during insertion of the medical device at least partially within the chamber. Thereafter, first and second deformable projections 1106 and 1108 removably retain the medical device within chamber 1104.

Medical device package 1100 also includes first and second frangible projections 1114 and 1116 (disposed within chamber 1104), respectively, and first and second rigid projections 1118 and 1120 (also disposed within chamber 1104), respectively. First and second frangible projections 1114 and 1116 are adapted to break upon a predetermined deformation (as described below with respect to FIG. 16D and step 1050 of FIG. 15). In addition, first and second frangible projections 1114 and 1116 are also adapted to (i) serve as a stop mechanism during the initial insertion of an unused medical device into medical device package 1100 such that the unused medical device does not become engaged with first and second rigid projections 1118 and 1120 and (ii) serve as a stop mechanism during engagement between a connector and a medical device. However, first and second rigid projections 1118 and 1120 are intended to engage (e.g., snap fit) into recesses 520 on medical device 510 upon re-insertion of a medical device 510 into package 1100 after use.

Next, at step 1020, proximal cap member 1112 is breached (e.g., ruptured) with connector 610, or alternatively is manually opened or removed, and at least a portion of the connector inserted into chamber 1104. The medical device 510 is then engaged by the connector 610, as set forth in step 1030 of FIG. 15 and depicted in FIG. 16B. As the medical device is engaged by the connector 610, the first and second deformable projections 1106 and 1108 reversibly bend away from the medical device 510 and toward body 1102.

Figure 16A:
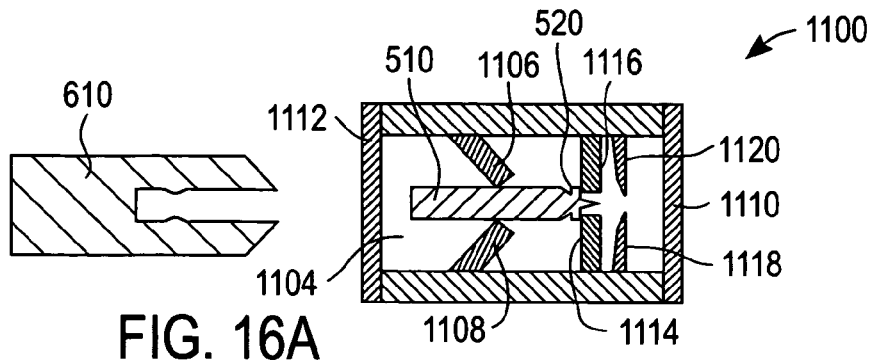
FIGS. 16A through 16E are schematic, cross-sectional side views depicting various stages of the process of FIG. 15.
Figure 16B:
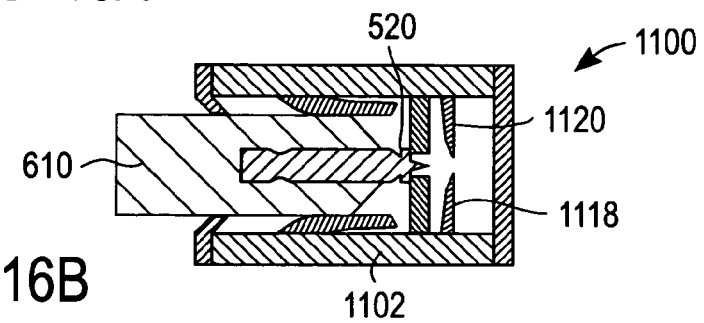
Figure 16C:
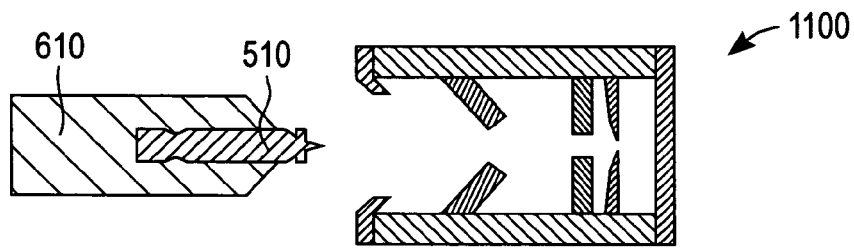

Subsequently, as set forth in step 1040 of FIG. 15, the connector and engaged medical device are extracted from chamber 1104 for use and the first and second deformable projections 1106 and 1108 bend back away from the body, as illustrated in FIG. 16C.

Figure 16D:
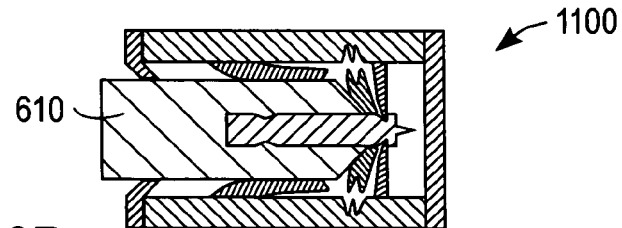
Figure 16E:
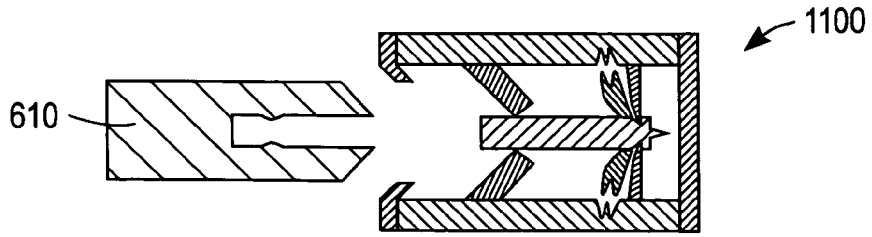

Thereafter, at step 1050, the connector and engaged medical device are inserted back into chamber 1104 such that first and second frangible projections 1114 and 1116 are broken and first and second rigid projections 1118 and 1120 engage with medical device 510 such that medical device 510 is prevented from being re-extracted from chamber 1104, thereby disabling the medical device from reuse (see FIG. 16D). The connector 610 is then disengaged from the medical device 510 and withdrawn from medical device package 1100, as set forth in step 1060 and as shown in FIG. 16E.

It is envisioned that during step 1050, the medical device 510 is disabled by virtue of the medical device breaking first and second frangible projections 1114 and 1116 and subsequently being engaged (e.g., snap-fit or lodged) into first and second rigid projections 1118 and 1120 such that the force required to remove the medical device 510 from the chamber is greater than the force required to disengage theconnector 610 from the medical device 510. Therefore, an attempt to re-extract the medical device with the connector would be unsuccessful since the connector would become disengaged from the medical device before sufficient force could be applied to extract the lodged medical device.

The force required to insert the medical device into the medical device package and disable the medical device is, for example, approximately 7N. As noted above, disablement of the medical device is a result of the medical device being engaged (e.g., snap fit) with the first and second rigid projections such that it cannot be re-extracted using the connector.

Processes according to embodiments of the present invention can be performed manually and/or automatically. Furthermore, such processes can be, for example, performed by an integrated device that combines an analytical meter and a connector in a configuration that provides for (i) a medical device to be extracted from a medical device package; (ii) a sample (e.g., a whole blood sample) to be obtained from a user and (iii) an analytical result (e.g., blood glucose concentration of the whole blood sample) to be determined, all by a single operation of the integrated device. Mechanical motions may be incorporated into a lancet cocking action, new test strip deployment and/or ejection.

Figure 17:
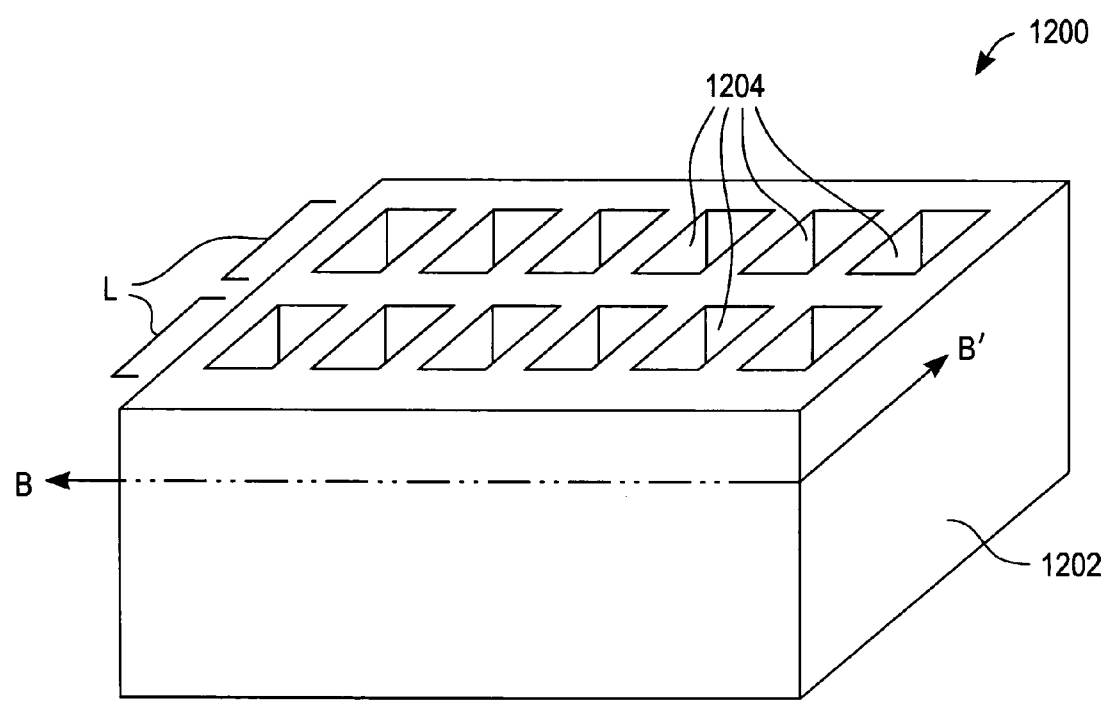
FIG. 17 is a simplified perspective view of a medical device package that includes a plurality of chambers according to a further embodiment of the present invention.
Figure 18A:
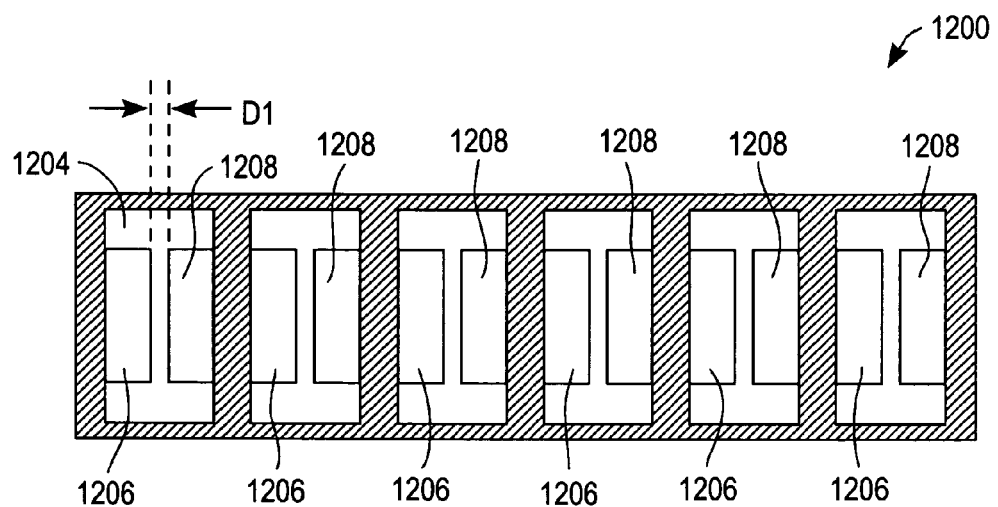
FIGS. 18A and 18B are simplified cross-sectional top views (along line B-B' of FIG. 17) of a portion of the medical device package of FIG. 17 without (FIG. 18A) and with (FIG. 18B) medical devices retained therein.
Figure 18B:
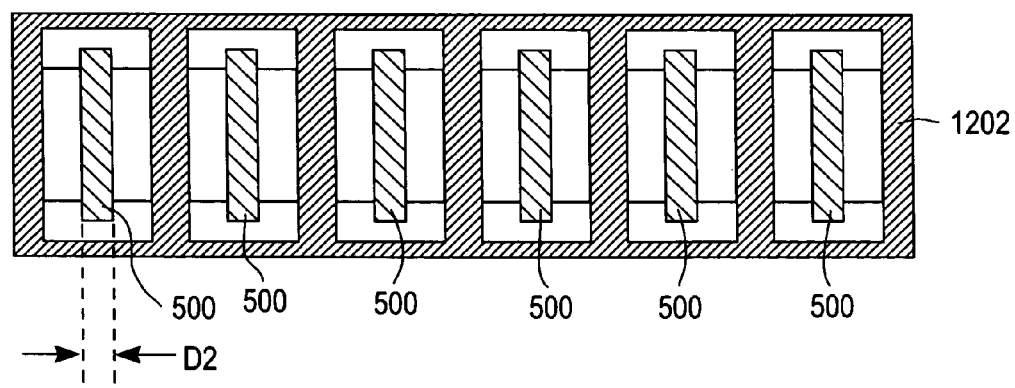

FIGS. 17, 18A and 18B depict a medical device package 1200 according to an exemplary embodiment of the present invention with FIG. 18B illustrating a medical device (i.e., medical device 500 of FIG. 5) contained within the medical device package 1200. Medical device package 1200 includes a body 1202 with a plurality of chambers 1204 defined therein. Although, for the purpose of explanation only, twelve chambers are depicted in the embodiment of FIG. 17, medical device package can have any suitable number of chambers. Each of the plurality of chambers has a first and second deformable projection 1206 and 1208, respectively, disposed therein, as shown in FIGS. 18A and 18B.

Chambers 1204 of medical device package 1200 are configured in a regular array consisting of two rows (labeled L in FIG. 17) of six chambers each. Although medical device package 1200 is depicted, for the purpose of explanation only, as including chambers configured in two rows, medical device packages according to embodiments of the present invention can include chambers configured in any suitable arrangement including, for example, a single row, a plurality of rows or any other suitable geometric configuration.

Since medical device package 1200 includes a plurality of chambers (e.g., 12 chambers), medical device package 1200 can contain an equal plurality of medical devices with one medical device being contained in each chamber. The regular array configuration of the chambers of medical device package 1200 facilitates integration into an analytical measurement system kit that includes (i) a compact measuring system, (ii) a medical device package (e.g., medical device package 1200, and (iii) medical devices.

The inclusion of deformable projections in medical device package 1200 enables reliable removal of medical devices contained in chambers 1204 without deleterious canting of the medical device as it is dispensed from chamber.

Referring to FIGS. 18A and 18B, distance D1 represents the distance between first and second deformable projections 1206 and 1208 when a medical device has not been inserted into chamber 1204. D1 can be any suitable distance, for example a distance in the range from about 0.1 millimeters to 5 millimeters and typically from about 0.25 to 0.5 millimeters. In general, distance D1 is sufficient to accommodate a medical device without damaging the medical device but sufficiently small to provide a secure fit when holding a medical device. Once apprised of the present disclosure, one skilled in the art will recognize that the distance (or gap) between deformable projections (e.g., distance D1 in FIG. 18A and gap G in FIG. 1) can also be zero or be a "negative" distance (i.e., the deformable projections can overlap one another) for medical device packages wherein the deformable projections are in a staggered configuration (e.g., the deformable projection configuration of FIG. 6E).

Distance D2 (see FIG. 18B) represents the distance between first and second deformable projections 1206 and 1208 when a medical device has been inserted into chamber 1204. Distance D2 is the thickness of medical device 500. Typical, but non-limiting, D2 distances are in the range from about 0.1 millimeters to 5 millimeters.

Medical device package 1200 can be formed, for example, as a unitary whole from molded plastic or can be assembled from multiple single-chamber medical device packages.

Figure 19:
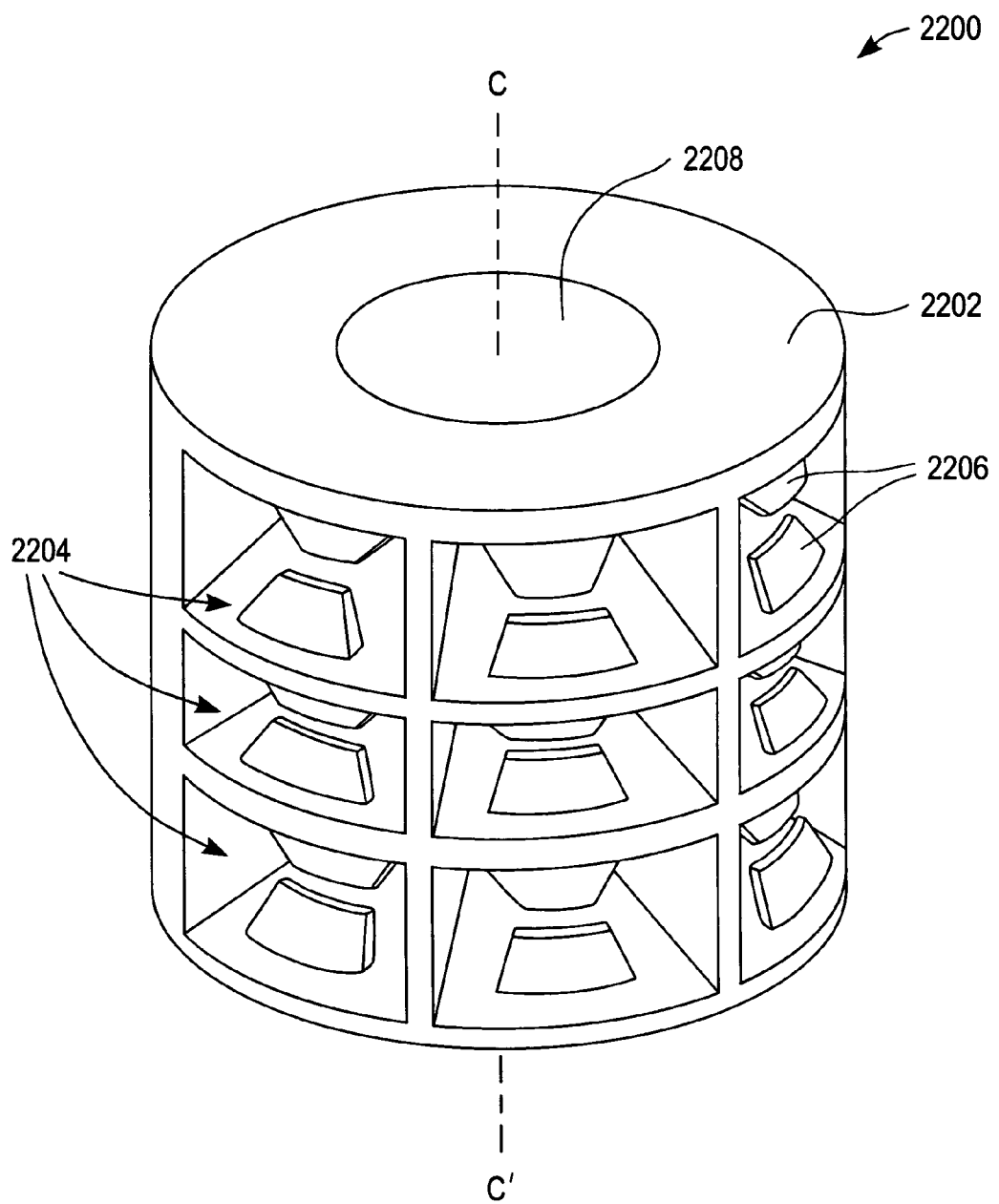
FIG. 19 is a simplified perspective view of an exemplary embodiment of a medical device package according to the present invention.

FIG. 19 illustrates a medical device package 2200 with a body 2202 and a plurality of chambers 2204 defined in body 2202. Chambers 2204 are arranged in a stacked regular radial array that is symmetrical about a plane that perpendicularly bisects longitudinal axis C-C' of medical device package 2200. Such symmetry is advantageous in affording leeway for the orientation of medical device package 2200 during insertion into an analysis instrument.

Medical device package 2200 also includes a plurality of deformable projections 2206 disposed within each of the plurality of chambers 2204. Although medical device package 2200 is depicted, for the purpose of explanation only, as including a plurality of deformable projections 2206 on top and bottom inner surface of the chambers 2204, medical device packages according to embodiments of the present invention can include a plurality of deformable projections 2206 in any suitable arrangement and locations within chambers 2204.

Furthermore, medical device package 2200 has a central cylindrically-shaped aperture 2208. Aperture 2208 extends through medical device package 2200 and is configured such that an analysis instrument (not shown) can employ aperture 2208 to mechanically secure medical device package 2200 during use.

Medical device package 2200 is beneficially constructed of molded plastic or other material that is impervious to air and/or air-borne bacteria, to provide a sterile-protective and puncture-resistant barrier. Suitable materials include, but are not limited to, polystyrene, polyethylene, polycarbonate and polyester.

For each of the medical device package exemplary embodiments described above, the deformable projection(s) securely retain(s) a medical device within the medical device package's chamber with insignificant deformation of the medical device. It is also noted that the orientation of a medical device within embodiments of medical device packages according to the present invention can vary from the orientation depicted in the figures.

Those skilled in the art will recognize that embodiments of medical device packages according to the present invention can be secondarily packaged for single use in, for example, a vial configured for dispensing the medical device packages. The secondary package may be constructed of material containing desiccant or may contain separately packaged desiccant for maintaining contents moisture free.

Once apprised of the present disclosure, one skilled in the art will also recognize that a variety of medical devices can be beneficially employed with embodiments of medical device packages according to the present invention. Such medical devices include, but are not limited to, integrated medical devices that include a combination of a test strip and a lancet, examples of which are described in the aforementioned International Application No. PCT/GB01/05634 (published as WO 02/49507 on Jun. 27, 2002) and U.S. patent application Ser. No. 10/143,399, both of which are fully incorporated herein by reference. One skilled in the art will also recognize that such test strips may have, but are not limited to, an electrochemical or photometric configuration. For illustrative purposes only, medical devices in various figures of the present disclosure were depicted as having an electrochemical configuration.

Moreover, those skilled in the art will appreciate that medical device packages according to embodiments of the present invention can be employed with medical device adapted for the measurement of, for example, glucose, ketones, glycated albumin, coagulation parameters and cholesterol of a sample.

In addition, one skilled in the art will also recognize that medical device packages according to the present invention may be contained within a combined sample collection and metering system designed for in-situ testing. Examples of such systems designed for in-situ testing are disclosed in International Patent Application No. PCT/US01/07169 (published as WO 01/64105 A1 on Sep. 7, 2001) and International Patent Application No. PCT/GB02/03772 (published as WO 03/015627 A1 on Feb. 27, 2003), each of which is fully incorporated herein by reference.

It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for extracting a medical device from a medical device package, the method comprising:

providing a medical device package with a medical device contained therein and a connector, the medical device package including:

a body with at least one chamber defined therein, a proximal end, and a distal end; and at least one frangible deformable projection within the at least one chamber, wherein the at least one frangible deformable projection is configured to deform resiliently upon contact with a medical device during insertion of the medical device at least partially within the chamber and, thereby, removably retain the medical device at least partially within the chamber in a predetermined extractable orientation and position;

inserting at least a portion of a connector into the chamber;

engaging the medical device with the connector such that the frangible deformable projection is broken; and extracting the engaged medical device from the chamber of the medical device package with the connector.

2. The method of claim 1, wherein the providing step includes providing a medical device package that includes a proximal cap member and a distal cap member and the inserting step includes inserting the connector into the chamber by breaching the proximal cap member.

3. The method of claim 1, wherein the extracting step includes extracting the medical device through the breached proximal cap member.

4. The method of claim 1, wherein the extracting step includes extracting the medical device by breaching the distal cap member and extracting the medical device through the breached distal cap member.

* * * * *